(12) United States Patent
Anderson et al.

(10) Patent No.: US 6,306,902 B1
(45) Date of Patent: Oct. 23, 2001

(54) OXALIPLATIN FORMULATIONS

(75) Inventors: Nicholas H. Anderson, Northumberland; Ross Blundell, Jesmond; Stephen Brown, Essex; David A. England; Martin R. Gray, both of Northumberland, all of (GB)

(73) Assignee: Sanofi-Synthelabo, Paris (FR)

( * ) Notice: Subject to any disclaimer, the term of this patent is extended or adjusted under 35 U.S.C. 154(b) by 0 days.

(21) Appl. No.: 09/255,087

(22) Filed: Feb. 22, 1999

(30) Foreign Application Priority Data

Feb. 25, 1998 (GB) .................................................. 9804013

(51) Int. Cl.⁷ .................................................. A61K 31/28
(52) U.S. Cl. .............................................................. 514/492
(58) Field of Search ............................................. 514/492

(56) References Cited

U.S. PATENT DOCUMENTS

| | | | |
|---|---|---|---|
| 4,169,846 | * | 10/1979 | Kidani et al. ..................... 260/429 R |
| 5,204,107 | * | 4/1993 | Tsurutani et al. ..................... 424/426 |
| 5,290,961 | * | 3/1994 | Okamoto et al. ..................... 556/137 |
| 5,298,642 | * | 3/1994 | Tozawa et al. ..................... 556/137 |
| 5,338,874 | * | 8/1994 | Nakanishi et al. ..................... 556/137 |
| 5,420,319 | * | 5/1995 | Okamoto et al. ..................... 556/137 |
| 5,633,016 | * | 5/1997 | Johnson ..................... 424/649 |
| 5,716,988 | * | 2/1998 | Ibrahim et al. ..................... 514/492 |

FOREIGN PATENT DOCUMENTS

| | | |
|---|---|---|
| 29896/95 | 3/1996 | (AU) . |
| 2128641 | * 2/1995 | (CA) . |
| 393575 | 10/1990 | (EP) . |
| 464210 | 1/1992 | (EP) . |
| 486998 | 5/1992 | (EP) . |
| 567438 | * 10/1993 | (EP) . |
| 617043 | * 9/1994 | (EP) . |
| 625523 | * 11/1994 | (EP) . |
| 715854 | * 6/1996 | (EP) . |
| 801070 | 10/1997 | (EP) . |
| WO93/09782 | 5/1993 | (WO) . |
| WO94/12193 | * 6/1994 | (WO) . |
| WO96/04904 | 2/1996 | (WO) . |

* cited by examiner

Primary Examiner—Jerome D. Goldberg
(74) Attorney, Agent, or Firm—Michael D. Alexander

(57) ABSTRACT

The invention relates to pharmaceutically stable oxaliplatin solution formulations, to the method of use thereof in the treatment of cancer tumors, to processes for the preparation of such formulations, and to a method for stabilizing solutions of oxaliplatin.

24 Claims, No Drawings

OXALIPLATIN FORMULATIONS

The invention relates to pharmaceutically stable oxaliplatin solution formulations, to the method of use thereof in the treatment of cancer tumors, to processes for the preparation of such formulations and to a method for stabilizing solutions of oxaliplatin.

Kidani et al,. U.S. Pat. No. 4,169,846, issued Oct. 2, 1979, disclose cis-platinum(II) complexes of isomers (cis-, trans-d, and trans-1 isomers) of 1,2-diaminocyclohexane represented by the general formula

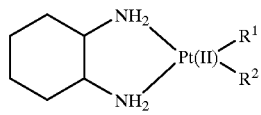

wherein the stereoisomerism of 1,2-diaminocyclohexane is cis, trans-d, or trans-1; and $R^1$ and $R^2$ represent halogen atoms, or $R^1$ and $R^2$ may, when taken together, form a group represented by the formula:

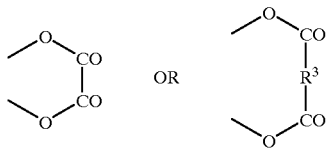

where $R^3$ represents a $>CH_2$ group, a $>CHCH_3$ or $>CHCH_2CH_3$ group. Cis-oxalato(trans-1-1,2-diaminocyclohexane)platinum (II) is specifically disclosed as example 4(i). The compounds are stated to possess anti-tumor activity.

Okamoto et al., U.S. Pat. No. 5,290,961, issued Mar. 1, 1994, disclose a process for preparing various platinum compounds including cis-oxalato(trans-1-1,2-cyclohexane-diamine)platinum (II). A similar disclosure is found in EP 617043, published Sep. 28, 1994.

Tozawa et al., U.S. Pat. No. 5,298,642, issued Mar. 29, 1994, disclose a process for optically resolving optically active platinum compounds by the use of chiral high perfomance liquid chromatography. The resolution of cis-oxalato(trans-d and trans-1-1,2-cyclohexane-diamine) platinum (II) is specifically disclosed. Nakanishi et al., U.S. Pat. No. 5,338,874, issued Aug. 16, 1994, disclose optically pure cis-oxalato(trans-1-1,2-cyclohexanediamine)platinum (II) and methods of preparing the same. A similar disclosure is found in EP 567438, published Oct. 27, 1993.

Okamoto et al., U.S. Pat. No. 5,420,319, issued May 30, 1995, disclose cis-oxalato(trans-1-1,2-cyclohexanediamine) platinum(II) having high optical purity and a process for preparing the same. A similar disclosure is found in EP 625523, published Nov. 23, 1994.

Masao et al., EP. 715854, published Jun. 12, 1996, disclose a process of compatibly administering cis-oxalato(1R, 2R-diaminocyclohexane)platinum(II), abbreviated as ("1-OHP"), with one or more existing carcinostatic substances and a carcinostatic substance comprising one or more compatible agents and 1-OHP.

Kaplan et al., Canadian patent application No. 2,128,641, published Feb. 12, 1995, disclose stable solutions of malonato platinum (II) antitumor agents, such as carboplatin, containing a stabilizing amount of 1,1-cyclobutanedicarboxylic acid or a salt thereof and a pharmaceutically acceptable carrier, said solution having a pH about 4 to about 8.

Ibrahim et al., WO94/12193, published Jun. 9, 1994, disclose a composition for jointly administering cisplatin and oxaliplatin, said composition being a freeze-dried composition containing cisplatin and oxaliplatin in a weight ratio of about 2:1 to 1:2 and a pharmaceutically acceptable chloride ion-free acidic buffer with a neutral substance being used as a ballast.

Tsurutani ET al., EP 486998, published May 27, 1992, disclose a slow-releasing composition comprising a platinum-containing anticancer agent bound to deacetylated chitin. A similar disclosure is found in U.S. Pat. No. 5,204,107, issued Apr. 20, 1993.

Ibrahim et al., Australian patent application No. 29896/95, published Mar. 7, 1996 (a patent family member of WO 96/04904, published Feb. 22, 1996), disclose a pharmaceutically stable preparation of oxaliplatin for parenteral administration consisting of a solution of oxaliplatin in water at a concentration in the range of 1 to 5 mg/mL and having a pH in the range of 4.5 to 6. A similar disclosure is found in U.S. Pat. No. 5,716,988, issued Feb. 10, 1998.

Johnson, U.S. Pat. No. 5,633,016, issued May 27, 1997, discloses pharmaceutical compositions comprising a compound of the camptothecin analog class and a platinum coordination compound and a pharmaceutically acceptable carrier or diluent. A similar disclosure is found in WO93/09782, published May 27, 1993.

Bach et al., EP 393575, published Oct. 24, 1990, disclose a combination therapy of therapeutically-effective amounts of a cytoprotective copolymer and one or more directly acting antineoplastic agents for the treatment of neoplastic disease.

Nakanishi et al., EP 801070, published Oct. 15, 1997, disclose a process for preparing various platinum complexes including cis-oxalato(trans-1-1,2-cyclohexane-diamine)Pt (II).

Oxaliplatin is currently available for both preclinical and clinical trials as a lyophilized powder which is reconstituted just before administration to a patient with water for injection or a 5% glucose solution, followed by dilution with a 5% glucose solution. Such a lyophilized product can, however, have several disadvantages. First of all, the lyophilization process can be relatively complicated and expensive to perform. In addition, the use of a lyophilized product requires that the product be reconstituted at the time of use, which provides an opportunity for there to be an error in choosing the appropriate solution for the reconstitution. For instance, the mistaken use of a 0.9% NaCl solution, which is a very common solution for the reconstitution of lyophilized products or for the dilution of liquid preparations, in the reconstitution of a lyophilized oxaliplatin product would be detrimental to the active ingredient in that a rapid reaction would occur, resulting not only in the loss of oxaliplatin, but in the precipitation of the species produced. Other disadvantages of a lyophilized product are:

(a) reconstitution of a lyophilized product increases the risk of microbial contamination over a sterile product which does not require reconstitution;

(b) there is a greater risk of sterility failure with a lyophilized product as compared to a solution product sterilized by filtration or by heat (terminal) sterilization; and (c) a lyophilized product has a potential for incomplete dissolution upon reconstitution resulting in particles which are undersirable for an injectable product.

It has been shown that in aqueous solutions oxaliplatin can, over time, degrade to produce as impurities varying amounts of diaquo DACH platin (formula I), diaquo

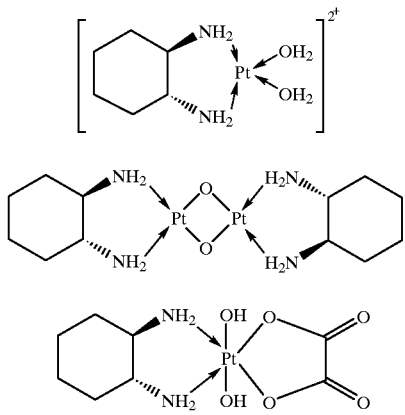

DACH platin dimer (formula II) and a platinum (IV) species (formula III). As the level of impurities present in any pharmaceutical formulation can, and in many cases does, affect the toxicological profile of the formulation, it would be desirable to develop a more stable solution formulation of oxaliplatin which either does not produce the above-described impurities at all or which produces such impurities in significantly smaller quantities than has heretofore been known.

Accordingly, a need exists for solution formulations of oxaliplatin in a ready-to-use (RTU) form, which overcome the above-described disadvantages and which are pharmaceutically stable over prolonged periods of storage, i.e., 2 years or more. It is accordingly an object of the present invention to overcome these disadvantages by providing a pharmaceutically stable oxaliplatin solution formulation in ready-to-use form.

More specifically, the present invention relates to a stable oxaliplatin solution formulation comprising oxaliplatin, an effective stabilizing amount of a buffering agent and a pharmaceutically acceptable carrier.

Oxaliplatin, which is known chemically as cis-oxalato (trans-1-1,2-cyclohexane-diamine)platinum (II) (can also be named as [SP-4-2]-(1R,2R)-(cyclohexane-1,2-diamine-k$^2$N, N' (oxalato(2-)-k$^2$O$^1$,O$^2$]platinum (II), (1,2-cyclohexanediamine-N,N')[ethanedioato(2-)-O,O']-[SP-4-2-(1R-trans)]-platinum, cis-[oxalato(1R,2R-cyclohexanediamine)platinum (II)], [(1R,2R)-1,2-cyclohexanediamine-N,N'][oxalato(2-)-O,O']platinum, [SP-4-2-(1R-trans)]-(1,2-cyclohexane-diamine-N,N') [ethanedioato(2-)-O,O']platinum, 1-OHP, and cis-oxalato (trans-1-1,2-diaminocyclo-hexane(platinum (II)), and has the chemical stricture shown below,

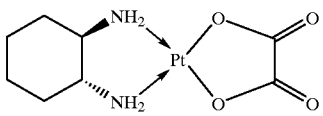

is a cytostatic antineoplastic agent which is useful in the therapeutic treatment of various types of susceptible cancers and tumors, such as, for example, colon cancer, ovarian cancer, epidermoid cancer, cancers of germinal cells (e.g., testicular, mediastina, pineal gland), non-small cell lung cancers, non-Hodgkins' lymphoma, breast cancer, cancers of the upper respiratory and digestive tracts, malignant melanoma, hepatocarcinoma, urothelial cancers, prostate cancers, small cell lung cancer, pancreatic cancer, gall bladder cancer, anal cancer, rectal cancer, bladder cancer, small intestine cancer, stomach cancer, leukemia and various other types of solid tumors.

The preparation, physical properties and beneficial pharmacological properties of oxaliplatin are described in, for example, U.S. Pat. Nos. 4,169,846, 5,290,961, 5,298,642, 5,338,874, 5,420,319 and 5,716,988, European patent application No. 715854 and Australian patent application No. 29896/95, the entire contents of which are herein incorporated by reference.

Oxaliplatin is conveniently present in the formulations of the present invention in the amount of from about 1 to about 7 mg/mL, preferably in the amount of from about 1 to about 5 mg/mL, more preferably in the amount of from about 2 to about 5 mg/mL, and in particular in the amount of about 5 mg/mL.

The term buffering agent as used herein means any acidic or basic agent which is capable of stabilizing oxaliplatin solutions and thereby preventing or retarding the formation of unwanted impurities such as diaquo DACH platin and diaquo DACH platin dimer. The term thus includes such agents as oxalic acid or alkali metal salts (e.,g., lithium, sodium, potassium and the like) of oxalic acid, and the like or mixtures thereof. The buffering agent is preferably oxalic acid or sodium oxalate and most preferably is oxalic acid.

The buffering agent is present in the formulations of the present invention in an effective stabilizing amount. The buffering agent is conveniently present in a molar concentration in the range of from about $5 \times 10^{-5}$ M to about $1 \times 10^{-2}$ M, preferably in a molar concentration in the range of about $5 \times 10^{-5}$ M to about $5 \times 10^{-3}$ M, more preferably in a molar concentration in the range of from about $5 \times 10^{-5}$ M to about $2 \times 10^{-3}$ M, most preferably in a molar concentration in the range of from about $1 \times 10^{-4}$ M to about $2 \times 10^{-3}$ M, especially in a molar concentration in the range of from about $1 \times 10^{-4}$ M to about $5 \times 10^{-4}$ M, and in particular in a molar concentration of about $2 \times 10^{-4}$ M or about $4 \times 10^{-4}$ M.

The term pharmaceutically acceptable carrier as used herein refers to the various solvents which can be employed in the preparation of the oxaliplatin solution formulations of the present invention. In general, the carrier will be water, one or more other suitable solvents, or a mixture of water and one or more other suitable solvents. Preferably, the carrier will be either water or a mixture of water and one or more other suitable solvents, and more preferably, the carrier is water. The water that is used is preferably pure water, i.e., sterile water for injection. Representative examples of the other suitable carriers (solvents) which can be utilized according to the present invention include polyalkylene glycols, such as polyethylene glycol, polypropylene glycol, polybutylene glycol and the like and mixtures thereof, ethanol, 1-vinyl-2-pyrrolidone polymer (povidone) and sugar solutions of pharmaceutically acceptable lactose, dextrose (glucose), sucrose, mannose, mannitol, cyclodextrin and the like or mixtures thereof.

The pH of the oxaliplatin solution formulations of the present invention is generally in the range of about 2 to about 6, preferably in the range of about 2 to about 5, and more preferably in the range of about 3 to about 4.5.

The oxaliplatin solution formulations of particular interest include those described in the accompanying examples and so formulations substantially as defined in the accompanying examples are provided as a further feature of the present invention.

As mentioned above, oxaliplatin is a cytostatic antineoplastic agent which is useful in the therapeutic treatment of various types of susceptible cancers and tumors. Thus, the present invention also provides a method for treating cancer or a solid tumor in a mammal which comprises administering to said mammal an effective amount of an oxaliplatin solution formulation of the present invention.

The present invention further relates to the use of an oxaliplatin solution formulation of the present invention for the preparation of a medicament for treating cancer or a solid tumor in a mammal.

The present invention further relates to a method for stabilizing a solution of oxaliplatin which comprises adding an effective stabilizing amount of a buffering agent to said solution. In a preferred aspect of this method, the solution is an aqueous (water) solution and the buffering agent is oxalic acid or an alkali metal salt thereof.

The present invention further relates to a process for preparing the oxaliplatin solution formulations of the present invention which comprises mixing a pharmaceutically acceptable carrier, a buffering agent and oxaliplatin.

A preferred process for preparing the oxaliplatin solution formulations of the present invention comprises the steps of:

(a) mixing a pharmaceutically acceptable carrier and a buffering agent, preferably at about 40° C.;

(b) dissolving oxaliplatin into said mixture, preferably at about 40° C.;

(c) cooling the mixture resulting from step (b), preferably to about room temperature, and making up to final volume with a pharmaceutically acceptable carrier;

(d) filtering the solution from step (c); and (e) optionally sterilizing the product resulting from step (d).

It should be noted that while the above process can conveniently be carried out either in the presence or absence of an inert atmosphere, it is preferably carried out under an inert atmosphere, such as nitrogen.

In a particularly preferred process for preparing the oxaliplatin solution formulations of the present invention the product resulting from step (d) above is sterilized by filtration or exposure to heat (terminal sterilization), preferably by exposure to heat.

The present invention further relates to a packaged pharmaceutical product comprising an oxaliplatin solution formulation of the present invention in a sealable container. The sealable container is preferably an ampoule, vial, infusion bag (pouch), or syringe. If the sealable container is a syringe, the syringe is preferably a graduated syringe which allows for the measured (metered) administration of the oxaliplatin solution formulations of the present invention, and in particular allows for the measured (metered) administration of such solution formulations directly into an infusion bag.

It should also be noted that the above-described oxaliplatin solution formulations of the present invention have, as is described more fully hereinbelow, been found to possess certain advantages over the presently known formulations of oxaliplatin.

Unlike the lyophilized powder form of oxaliplatin, the ready-to-use formulations of the instant invention are made by a less expensive and less complicated manufacturing process.

In addition, the formulations of the instant invention require no additional preparation or handling, e.g., reconstitution, before administration. Thus, there is no chance that an error will occur in choosing the appropriate solvent for the reconstitution as there is with a lyophilized product.

The formulations of the instant invention have also been found to be more stable during the manufacturing process than the previously known aqueous formulations of oxaliplatin which means that less impurities, e.g., diaquo DACH platin and diaquo DACH platin dimer, are produced in the instant formulations than in the previously known aqueous formulations of oxaliplatin.

The formulations of the instant invention can also be sterilized by filtration or exposure to heat (terminal sterilization) without adversely affecting the quality of the formulations.

These and other advantages of the formulations of the instant invention will become more evident upon further consideration of the instant specification and claims.

The formulations of the present invention are generally administered to patients, which include, but are not limited to, mammals, such as, for example, man, by conventional routes well known in the art. For example, the formulations can be administered to patients parenterally (e.g., intravenously, intraperitoneally and the like). The formulations are preferably administered parenterally and in particular are administered intravenously. When infused intravenously, the formulation is generally administered over a period of up to 5 days, preferably over a period of up to 24 hours and more preferably over a period of 2 to 24 hours.

It will also be apparent to those skilled in the art that the oxaliplatin solution formulations of the present invention can be administered with other therapeutic and/or prophylactic agents and/or medicaments that are not medically incompatible therewith.

The percentage of active component, i.e., oxaliplatin, in the formulations of the present invention may be varied so that a suitable dosage is obtained. The dosage administered to a particular patient is variable depending upon the clinician's judgment using as criteria: the route of administration, the duration of treatment, the size, age and physical condition of the patient, the severity of the condition, the potency of the active component and the patient's response thereto. An effective dosage amount of the active component can thus readily be determined by the clinician after a consideration of all criteria and using his best judgment on the patient's behalf. In general, the active component of the formulations of the present invention can be administered to patients in doses ranging from about 10 mg/m$^2$ to about 250 mg/m$^2$, more preferably from 20 mg/m$^2$ to about 200 mg/m$^2$ and most preferably from about 30 mg/m$^2$ to about 180 mg/m$^2$. The preferred dosing regimen for oxaliplatin includes administration of repeated dosages of oxaliplatin in cycles of 1 to 5 days at intervals of 1 to 5 weeks.

The following examples will further illustrate the invention without, however, limiting it thereto. All temperatures are expressed in degrees Celsius (° C.).

The formulations of Examples 1–14 set forth in Tables 1A and 1B were prepared by the following general procedure:

Dispense hot water (40° C.) for injection (W.F.I.) and bubble through with filtered nitrogen for approximately 30 minutes.

Transfer an appropriate amount of the W.F.I. required to a suitable mixing vessel while maintaining under nitrogen. Set aside the remaining W.F.I. to make up to the final volume.

Weigh appropriate buffering agent (either in the form of a solid or preferably in the form of an aqueous buffer solution of the appropriate molarity) into a suitable container and transfer to the mixing vessel (rinse container with part of the remaining W.F.I.). Mix, e.g., on a magnetic stirrer/hotplate, for approximately 10 minutes or, if necessary, until all of the solids have dissolved, while keeping the temperature of the solution at 40° C.

Weigh oxaliplatin into a suitable container and transfer to the mixing vessel (rinse container with part of the remaining hot (40° C.) W.F.I.). Mix, e.g., on a magnetic stirrer/hotplate, until all of the solids have dissolved, while keeping the temperature of the solution at 40° C.

Allow the solution to cool to room temperature, then make up to the final volume with the remaining W.F.I.

Filter the solution under vacuum through a 0.22 μm filter (e.g., a millipore type GV, 47 mm diameter filter).

Fill the solution under nitrogen into suitable sterilized and sealable containers (e.g., vials or ampoules) using a filler unit, e.g., a sterile 0.2 μm disposable hydrophilic filler unit (Minisart—NML, Sartorius), with the sealable containers being purged with nitrogen before filling and the headspace being purged with nitrogen before sealing.

Autoclave, i.e., terminally sterilize, the solution for 15 minutes at 121° C. using, for example, an SAL (PD270) autoclave.

It should be noted that while the above process has preferably been carried out under an inert atmosphere, such as nitrogen, the formulations of the instant invention can also be conveniently prepared in the absence of such an inert atmosphere.

TABLE 1A

| Ingredient | Example 1 0.00001 M sodium oxalate | Example 2 0.00005 M sodium oxalate | Example 3 0.0001 M sodium oxalate | Example 4 0.0003 M sodium oxalate | Example 5 0.0005 M sodium oxalate | Example 6 0.001 M sodium oxalate | Example 7 0.002 M sodium oxalate |
|---|---|---|---|---|---|---|---|
| Oxaliplatin | 5.000 g | 5.000 g | 5.000 g | 5.000 g | 5.000 g | 5.000 g | 5.000 g |
| Water for injection | 1000 mL | 1000 mL | 1000 mL | 1000 mL | 1000 mL | 1000 mL | 1000 mL |
| Amount sodium oxalate | 1.340 mg | 6.700 mg | 13.40 mg | 40.20 mg | 67.00 mg | 134.00 mg | 268.00 mg |

Note: The sealable containers which were utilized for the formulations of Examples 1–7 were 20 mL clear glass ampoules.

TABLE 1B

| Ingredient | Example 8 0.00001 M oxalic acid | Example 9 0.00005 M oxalic acid | Example 10 0.0001 M oxalic acid | Example 11 0.0003 M oxalic acid | Example 12 0.0005 M oxalic acid | Example 13 0.001 M oxalic acid | Example 14 0.002 M oxalic acid |
|---|---|---|---|---|---|---|---|
| Oxaliplatin | 5.000 g | 5.000 g | 5.000 g | 5.000 g | 5.000 g | 5.000 g | 5.000 g |
| Water for injection | 1000 mL | 1000 mL | 1000 mL | 1000 mL | 1000 mL | 1000 mL | 1000 mL |
| Amount Oxalic Acid* | 1.260 mg | 6.300 mg | 12.60 mg | 37.80 mg | 63.00 mg | 126.10 mg | 252.10 mg |

Note: The sealable containers which were utilized for the formulations of Examples 8–14 were 20 mL clear glass ampoules.
*Oxalic acid is added as the dihydrate; the weights shown here are of oxalic acid dihydrate added.

The formulations of Examples 15 and 16 set forth in Table 1C were prepared in a manner similar to that described above for the preparation of the formulations of Examples 1–14.

TABLE 1C

| Ingredient | Example 15 0.0002 M oxalic acid | Example 16 0.0004 M oxalic acid |
|---|---|---|
| Oxaliplatin | 7.500 g | 7.500 g |
| Water for injection | 1500 mL | 1500 mL |
| Amount Oxalic Acid* | 37.82 mg | 75.64 mg |

Note:
The sealable containers which were utilized for the formulations of Examples 15–16 were 20 mL clear glass ampoules.
*Oxalic acid is added as the dihydrate; the weights shown here are of oxalic acid dihydrate added.

The formulation of Example 17 set forth in Table 1D was prepared in a manner similar to that described above for the preparation of the formulations of Examples 1–14, except that: (a) the solution was filled into the sealable containers in the absence of nitrogen (i.e., in the presence of oxygen); (b) the sealable containers were not purged with nitrogen before filling; (c) the headspace was not purged with nitrogen before sealing the containers; and (d) the sealable containers were vials rather than ampoules.

TABLE 1D

| Ingredient | Example 17 0.0002 M oxalic acid |
|---|---|
| Oxaliplatin | 10.000 g |
| Water for injection | 2000 mL |
| Amount Oxalic Acid* | 50.43 mg |

TABLE 1D-continued

| Ingredient | Example 17 0.0002 M oxalic acid |
|---|---|

Note:
1000 mL of the solution formulation of Example 17 was filled into 5 mL clear glass vials (4 mL of solution per vial) which were sealed with a West Flurotec stopper [hereinafter referred to as Example 17(a)] and the remaining 1000 mL of the solution formulation of Example 17 was filled into 5 mL clear glass vials (4 mL of solution per vial) which were sealed with a Helvoet Omniflex stopper [hereinafter referred to as Example 17(b)].
*Oxalic acid is added as the dihydrate; the weights shown here are of oxalic acid dihydrate added.

Preparation of 0.0005 M Sodium Oxalate Buffer

Dispense greater than 2000 mL of water for injection (W.F.I.) and bubble filtered nitrogen through the water for approximately 30 minutes.

Transfer 1800 ml of the W.F.I. into a 2000 mL Schott bottle and maintain under an $N_2$ cloud. Set aside the remainder (200 mL) to make up the final volume.

Weigh sodium oxalate (134.00 mg) into a weighing boat and transfer into the Schott bottle (rinsing with approximately 50 mL of W.F.I.).

Stir the mixture on a magnetic stirrer/hotplate until all of the solids have dissolved.

Transfer the solution to a 2000 mL volumetric flask and make up to 2000 mL with W.F.I. and then purge the headspace of the flask with nitrogen before stoppering.

The various other sodium oxalate and oxalic acid buffer solutions set forth in Tables 1A, 1B, 1C and 1D were prepared following a procedure similar to that described above for the preparation of the 0.0005 M sodium oxalate buffer solution.

EXAMPLE 18

For comparative purposes, an aqueous oxaliplatin formulation, such as those disclosed in Australian patent application No. 29896/95, published Mar. 7, 1996, was prepared as follows:

Dispense greater than 1000 mL of water for injection (W.F.I.) and bubble filtered nitrogen through the solution for approximately 30 minutes. Stir on a magnetic stirrer/hotplate and heat the W.F.I. to 40° C.

Transfer 800 mL of W.F.I. into a 1000 mL Schott bottle and maintain under an $N_2$ cloud. Set aside the remainder of W.F.I. (200 mL) to make up the final volume.

Weigh oxaliplatin (5.000 g) into a small glass beaker (25 mL) and transfer into a Schott bottle, rinsing the beaker with approximately 50 mL of hot W.F.I.

Stir the mixture on a magnetic stirrer/hotplate until all of the solids have dissolved, while keeping the temperature at 40° C.

Allow the solution to cool to room temperature, then transfer it to a 1000 mL volumetric flask and make up the flask to 1000 mL with cool (approximately 20° C.) W.F.I.

The solution was filtered into a 1000 mL flask through a Millipore type GV, 47 mm diameter, 0.22 $\mu$m filter using a vacuum line.

The solution was then filled into washed and sterilized 20 mL glass ampoules using a sterile 1.2 $\mu$m disposable hydrophilic filter unit (Minisart—NML, Sartorius). The ampoules were purged with nitrogen before filling and the headspace was purged with nitrogen before sealing.

Twenty-three of the ampoules were kept unautoclaved [hereinafter referred to as Example 18(a)], i.e., they were not terminally sterilized, and the remaining 27 ampoules [hereinafter referred to as Example 18(b)] were autoclaved for 15 minutes at 121° C. using a SAL (PD 270) autoclave.

Stability Studies

In the stability studies described hereinbelow, the following chromatographic methods were utilized to evaluate the stability of the various oxaliplatin solution formulations.

The percentage of the platinum (IV) species, the unspecified impurities and oxaliplatin was determined by high performance liquid chromatography (HPLC) using a Hypersil™ C18 column and a mobile phase containing dilute orthophosphoric acid and acetonitrile. Under these conditions, the platinum (IV) species and oxaliplatin had retention times of approximately 4.6 and 8.3 minutes, respectively.

The percentage of the diaquo DACH platin and the diaquo DACH platin dimer, as well as the unspecified impurities referred to in Tables 4–8, was determined by HPLC using a Hypersil™ BDS C18 column and a mobile phase containing phosphate buffer and acetonitrile. Under these conditions, the diaquo DACH platin and diaquo DACH platin dimer had retention times of approximately 4.3 and 6.4 minutes respectively, whereas oxaliplatin eluted with the solvent front.

Oxaliplatin in Various Aqueous Buffers

A 2 mg/mL oxaliplatin solution in a 0.0005 M sodium oxalate buffer solution (0.0670 mg/mL of sodium oxalate) was prepared in a manner similar to that described above for the preparation of Examples 1–14 and the stability of this solution , as well as various other oxaliplatin solutions (2 mg/mL) in a range of commonly used aqueous buffer solutions, was analyzed. The results obtained when each solution was stressed for approximately one month at 40° C. are given in Table 2.

TABLE 2

| Buffer | Initial Assay (% of theoretical) | Assay after ~ 1 month at 40° C. (% of theoretical) |
|---|---|---|
| 0.0005 M sodium oxalate | 102.1 | 98.8 |
| 0.1 M citrate, pH 3 | 100.4 | 63.6 |
| 0.1 M citrate, pH 5 | 95.8 | 24.7 |
| 0.1 M acetate, pH 5 | 100.3 | 76.5 |
| 0.1 M tris, pH 7 | 80.1 | 1.0 |
| 0.1 M tris, pH 9 | 22.1 | 0.0 |
| 0.1 M glycine, pH 3 | 96.8 | 0.1 |
| 0.1 M glycine, pH 9 | 49.7 | 0.0 |
| 0.1 M phosphate, pH 7 | 98.4 | 19.0 |

These results demonstrate that oxaliplatin was not stable in various commonly used aqueous buffer solutions, such as citrate, acetate, tris, glycine and phosphate buffers when the solution was stressed. However, it was discovered that stable aqueous solutions of oxaliplatin can be obtained when a buffering agent, such as oxalic acid or an alkali metal salt thereof, e.g., sodium oxalate, is utilized.

Autoclaved Oxaliplatin Solutions in Oxalate Buffer

A 2 mg/mL oxaliplatin solution in a 0.01 M sodium oxalate buffer (1.340 mg/mL of sodium oxalate), with a sample solution pH of approximately 4, was prepared in a manner similar to that described above for the preparation of Examples 1–14. The stability results for this solution after 0, 1, 2 and 3 autoclave cycles (with each cycle lasting 15 minutes at 121° C.) are summarized in Table 3.

TABLE 3

| Number of Autoclave Cycles | Assay (mg/mL) | Diaquo DACH Platin (% w/w) | Diaquo DACH Platin Dimer (% w/w) | Platinum (IV) Species (% w/w) | Total Impurities (% w/w) |
|---|---|---|---|---|---|
| 0 | 2.03 | ND <0.01 | ND <0.01 | 0.02 | 0.02 |
| 1 (15 min/ 121° C.) | 1.96 | ND <0.01 | ND <0.01 | 0.06 | 0.05 |
| 2 (30 min/ 121° C.) | 2.01 | ND <0.01 | ND <0.01 | 0.09 | 0.10 |
| 3 (45 min/ 121° C.) | 1.97 | ND <0.01 | ND <0.01 | 0.12 | 0.15 |

ND = None Detected

A 5 mg/mL oxaliplatin solution in a 0.0002 M oxalic acid buffer and a 5 mg/mL oxaliplatin solution in a 0.0004 M oxalic acid buffer were prepared, both in the presence and the absence of oxygen, in a manner similar to that described above for the preparation of Examples 1–16. The stability results for these solutions after 0, 1, 2 and 3 autoclave cycles (with each cycle lasting for 15 minutes at 121° C.) and three autoclave cycles of 15 minutes at 121° C. and a fourth autoclave cycle lasting for 75 minutes at 121° C. (total 120 minutes) are summarized in Table 3A.

TABLE 3A

| 5 mg/mL Oxaliplatin in: | Time at 121° C. (min) | Diaquo DACH Platin (% w/w) | Diaquo DACH Platin Dimer (% w/w) | Pt (IV) Species (% w/w) | Total Unspecified Impurities (% w/w) | Total Chromatographic Impurites (% w/w) |
|---|---|---|---|---|---|---|
| 0.0002M oxalic acid manufactured under nitrogen | 0 | 0.10 | ND <0.01 | ND <0.003 | ND <0.03 | 0.10 |
| | 15 (1 cycle) | 0.13 | ND <0.01 | ND <0.003 | T <0.03 | 0.13 |
| | 30 (2 cycles) | 0.10 | ND <0.01 | T <0.01 | T <0.03 | 0.10 |
| | 45 (3 cycles) | 0.10 | ND <0.01 | T <0.01 | T <0.03 | 0.10 |
| | 120 (4 cycles) | 0.09 | ND <0.01 | T <0.01 | T <0.03 | 0.09 |
| 0.0002M oxalic acid manufactured under oxygen | 0 | 0.14 | ND <0.01 | 0.02 | T <0.05 | 0.16 |
| | 15 (1 cycle) | 0.13 | ND <0.0l | 0.01 | T <0.05 | 0.14 |
| | 30 (2 cycles) | 0.11 | ND <0.01 | T <0.01 | T <0.05 | 0.14 |
| | 45 (3 cycles) | 0.12 | ND <0.01 | T <0.01 | T <0.05 | 0.15 |
| | 120 (4 cycles) | 0.12 | ND <0.01 | T <0.01 | T <0.05 | 0.16 |
| 0.0004M oxalic acid manufactured under nitrogen | 0 | 0.14 | ND <0.01 | T <0.01 | T <0.05 | 0.14 |
| | 15 (1 cycle) | 0.14 | ND <0.01 | T <0.01 | T <0.05 | 0.14 |
| | 30 (2 cycles) | 0.12 | ND <0.01 | T <0.01 | T <0.05 | 0.12 |
| | 45 (3 cycles) | 0.11 | ND <0.01 | T <0.01 | T <0.05 | 0.11 |
| | 120 (4 cycles) | 0.12 | ND <0.01 | T <0.01 | T <0.05 | 0.12 |
| 0.0004M oxalic acid manufactured under oxygen | 0 | 0.13 | ND <0.01 | 0.02 | ND <0.05 | 0.15 |
| | 15 (1 cycle) | 0.13 | ND <0.01 | 0.01 | T <0.05 | 0.14 |
| | 30 (2 cycles) | 0.13 | ND <0.01 | 0.01 | T <0.05 | 0.14 |
| | 45 (3 cycles) | 0.11 | ND <0.01 | 0.01 | T <0.05 | 0.12 |
| | 120 (4 cycles) | 0.11 | ND <0.01 | T <0.01 | T <0.05 | 0.11 |

ND = Not detected
T = Trace

The above results demonstrate that the oxaliplatin solution formulations of the present invention can be terminally sterilized without adversely affecting the quality of the formulation.

Stability Studies for Formulations of Examples 1–17

The oxaliplatin solution formulations of Examples 1–14 were stored for up to 6 months at 40° C. and the stability results of this study are summarized in Tables 4 and 5.

TABLE 4

| Example No. | Sodium Oxalate Molarity | Time at 40° C. | Measured pH | Diaquo DACH Platin (% w/w) | Diaquo DACH Platin Dimer (% w/w) | Unspecified Impurities (% w/w) |
|---|---|---|---|---|---|---|
| 1 | 0.00001 | initial | 5.26 | 0.20 | 0.15 | 0.03 |
| | 0.00001 | 1 month | 5.25 | 0.21 | 0.15 | 0.13 |
| 2 | 0.00005 | initial | 5.75 | 0.18 | 0.12 | 0.04 |
| | 0.00005 | 1 month | 5.32 | 0.16 | 0.11 | 0.12 |
| 3 | 0.0001 | initial | 5.64 | 0.14 | 0.11 | 0.05 |
| | 0.0001 | 1 month | 5.33 | 0.14 | 0.08 | 0.11 |
| 4 | 0.0003 | initial | 5.77 | 0.09 | 0.07 | 0.06 |
| | 0.0003 | 1 month | 5.74 | 0.10 | 0.07 | 0.10 |
| 5 | 0.0005 | initial | 5.71 | 0.06 | 0.06 | 0.06 |
| | 0.0005 | 1 month | 5.68 | 0.08 | 0.05 | 0.08 |
| 6 | 0.001 | initial | 5.48 | 0.04 | 0.04 | 0.06 |
| | 0.001 | 1 month | 5.85 | 0.05 | 0.03 | 0.07 |
| 7 | 0.002 | initial | 5.90 | 0.06 | 0.03 | 0.06 |
| | 0.002 | 1 month | 6.02 | 0.03 | trace <0.03 | 0.05 |

TABLE 5

| Example No. | Oxalic Acid Molarity | Time at 40° C. | Measured pH | Diaquo DACH Platin (% w/w) | Diaquo DACH Platin Dimer (% w/w) | Unspecified Impurities (% w/w) |
|---|---|---|---|---|---|---|
| 8 | 0.00001 | initial | 5.92 | 0.22 | 0.17 | 0 |
| | 0.00001 | 1 month | 5.23 | 0.27 | 0.19 | 0.04 |
| 9 | 0.00005 | initial | 4.40 | 0.15 | 0.05 | 0 |
| | 0.00005 | 1 month | 4.71 | 0.16 | 0.03 | 0.02 |
| 10 | 0.0001 | initial | 3.70 | 0.13 | trace <0.03 | 0 |
| | 0.0001 | 1 month | 4.10 | 0.12 | ND <0.01 | 0.02 |
| | 0.0001 | 3 month | 3.94 | 0.13 | ND <0.01 | trace <0.03 |
| | 0.0001 | 6 month | 4.17 | 0.13 | ND <0.01 | trace <0.03 |
| 11 | 0.0003 | initial | 3.47 | 0.13 | ND <0.01 | 0 |
| | 0.0003 | 1 month | 3.52 | 0.11 | ND <0.01 | 0.01 |
| | 0.0003 | 3 month | 3.56 | 0.12 | ND <0.01 | trace <0.03 |
| | 0.0003 | 6 month | 3.48 | 0.10 | ND <0.01 | trace <0.03 |
| 12 | 0.0005 | initial | 3.28 | 0.13 | ND <0.01 | 0 |
| | 0.0005 | 1 month | 3.35 | 0.10 | ND <0.01 | 0.01 |
| | 0.0005 | 3 month | 3.30 | 0.13 | ND <0.01 | trace <0.03 |
| | 0.0005 | 6 month | 3.34 | 0.11 | ND <0.01 | trace <0.03 |
| 13 | 0.001 | initial | 3.05 | 0.13 | ND <0.01 | 0 |
| | 0.001 | 1 month | 3.02 | 0.11 | ND <0.01 | 0.01 |
| 14 | 0.002 | initial | 2.85 | 0.14 | ND <0.01 | 0 |
| | 0.002 | 1 month | 2.70 | 0.13 | ND <0.01 | 0.01 |

ND = None Detected.

The oxaliplatin solution formulations of Examples 15 and 16 were stored for up to 9 months at 25° C./60% relative humidity (RH) and 40° C./75% relative humidity (RH) and the stability results of this study are summarized in Table 6.

TABLE 6

| Example No. | Oxalic Acid Molarity | Time | Measured pH | Diaquo DACH Platin (% w/w) | Diaquo DACH Platin Dimer (% w/w) | Platinum (IV) Species (% w/w) | Total Chromatographic Impurities (% w/w) |
|---|---|---|---|---|---|---|---|
| 15 | 0.0002 | Initial | 3.83 | 0.10 | ND <0.01 | ND <0.003 | 0.10 |
| | 0.0002 | 1 Month (25° C./60% RH) | 3.75 | 0.12 | ND <0.01 | Trace <0.01 | 0.12 |
| | 0.0002 | 1 Month (40° C./75% RH) | 3.78 | 0.13 | ND <0.01 | Trace <0.01 | 0.13 |
| | 0.0002 | 3 Months (25° C./60% RH) | 4.13 | 0.10 | ND <0.01 | Trace <0.01 | 0.10 |
| | 0.0002 | 3 Months (40° C./75% RH) | 4.16 | 0.12 | ND <0.01 | Trace <0.01 | 0.12 |
| | 0.0002 | 6 Months (25° C./60% RH) | 3.45 | 0.12 | ND <0.01 | Trace <0.01 | 0.12 |
| | 0.0002 | 6 Months (40° C./75% RH) | 3.52 | 0.11 | ND <0.01 | Trace <0.01 | 0.11 |
| | 0.0002 | 9 Months (25° C./60% RH) | 3.62 | 0.14 | ND <0.01 | Trace <0.01 | 0.14 |
| | 0.0002 | 9 Months (40° C./75% RH) | 3.64 | 0.11 | ND <0.01 | Trace <0.01 | 0.11 |
| 16 | 0.0004 | Initial | 3.45 | 0.10 | ND <0.01 | Trace <0.01 | 0.10 |
| | 0.0004 | 1 Month (25° C./60% RH) | 3.40 | 0.13 | ND <0.01 | Trace <0.01 | 0.13 |
| | 0.0004 | 1 Month (40° C./75% RH) | 3.44 | 0.12 | ND <0.01 | Trace <0.01 | 0.12 |
| | 0.0004 | 3 Months (25° C./60% RH) | 3.59 | 0.11 | ND <0.01 | Trace <0.01 | 0.11 |
| | 0.0004 | 3 Months (40° C./75% RH) | 3.71 | 0.12 | ND <0.01 | Trace <0.01 | 0.12 |
| | 0.0004 | 6 Months (25° C./60% RH) | 3.24 | 0.11 | ND <0.01 | Trace <0.01 | 0.11 |
| | 0.0004 | 6 Months (40° C./75% RH) | 3.26 | 0.11 | ND <0.01 | Trace <0.01 | 0.11 |
| | 0.0004 | 9 Months (25° C./60% RH) | 3.26 | 0.12 | ND <0.01 | Trace <0.01 | 0.12 |
| | 0.0004 | 9 Months (40° C./75% RH) | 3.31 | 0.12 | ND <0.01 | Trace <0.01 | 0.12 |

ND = None Detected.

The oxaliplatin solution formulations of Examples 17(a) and 17(b) were stored for up to 1 month at 25° C./60% relative humidity (RH) and 40° C./75% relative humidity (RH) and the stability results of this study are summarized in Table 7.

The results of these stability studies demonstrate that buffering agents, such as sodium oxalate and oxalic acid are extremely effective in controlling the levels of impurities, such as diaquo DACH platin and diaquo DACH platin dimer, in the solution formulations of the present invention.

TABLE 7

| Example No. | Oxalic Acid Molarity | Time | Measured pH | Diaquo DACH Platin (% w/w) | Diaquo DACH Platin Dimer (% w/w) | Platinum (IV) Species (% w/w) | Unspecified Impurities (% w/w) |
|---|---|---|---|---|---|---|---|
| 17(a) | 0.0002 | Initial | 3.81 | 0.13 | ND <0.01 | 0.02 | Trace <0.05 |
| | 0.0002 | 1 Month (25° C./60% RH) | 3.82 | 0.12 | ND <0.01 | 0.03 | Trace <0.05 |
| | 0.0002 | 1 Month (40° C./75% RH) | 3.79 | 0.13 | ND <0.01 | 0.05 | 0.13 |
| 17(b) | 0.0002 | Initial | 3.53 | 0.14 | ND <0.01 | 0.03 | 0.05 |
| | 0.0002 | 1 Month (25° C./60% RH) | 3.72 | 0.12 | ND <0.01 | 0.07 | 0.16 |
| | 0.0002 | 1 Month (40° C./75% RH) | 3.73 | 0.12 | ND <0.01 | 0.09 | 0.07 |

ND = None Detected.

Stability of Comparative Example 18

The unbuffered oxaliplatin solution formulation of Example 18(b) was stored for one month at 40° C. and the results of this stability study are summarized in Table 8.

TABLE 8

| Time at 40 °C. | Measured pH | Diaquo DACH Platin (% w/w) | Diaquo DACH Platin Dimer (% w/w) | Unspecified Impurities (% w/w) |
|---|---|---|---|---|
| Initial | 5.47 | 0.27 | 0.16 | 0.04 |
| 1 Month | 5.27 | 0.23 | 0.16 | 0.14 |

In addition three separate batches of an aseptically prepared (i.e., prepared under aseptic conditions but not autoclaved) solution product (2 mg/mL of oxaliplatin in pure water) were prepared in a manner similar to that described in Example 18(a) and the batches were stored at ambient temperature for approximately 15 months. The results of this stability study are summarized in Table 9.

TABLE 9

| Batch No. | Temperature | Diaquo DACH Platin (% w/w) | Diaquo DACH Platin Dimer (% w/w) |
|---|---|---|---|
| A | Ambient | 0.34 | 0.29 |
| B | Ambient | 0.36 | 0.28 |
| C | Ambient | 0.38 | 0.29 |

What is claimed is:

1. A stable oxaliplatin solution formulation comprising a therapeutically effective amount of oxaliplatin, an effective stabilizing amount of a buffering agent and a pharmaceutically acceptable carrier wherein the buffering agent is oxalic acid or an alkali metal salt thereof.

2. A formulation according to claim 1 wherein the pharmaceutically acceptable carrier is water and the buffering agent is oxalic acid or an alkali metal salt thereof.

3. A formulation according to claim 2 wherein the buffering agent is oxalic acid or sodium oxalate.

4. A formulation according to claim 3 wherein the buffering agent is oxalic acid.

5. The formulation according to claim 1 wherein the amount of buffering agent is a molar concentration in the range of from
   (a) about $5 \times 10^{-5}$ M to about $1 \times 10^{-2}$ M,
   (b) about $5 \times 10^{-5}$ M to about $5 \times 10^{-3}$ M,
   (c) about $5 \times 10^{-5}$ M to about $2 \times 10^{-3}$ M,
   (d) about $1 \times 10^{-4}$ M to about $2 \times 10^{-3}$ M, or
   (e) about $1 \times 10^{-4}$ M to about $5 \times 10^{-4}$ M.

6. A formulation according to claim 5 wherein the amount of buffering agent is a molar concentration in the range of from about $1 \times 10^{-4}$ M to about $5 \times 10^{-4}$ M.

7. A formulation acording to claim 6 wherein the amount of buffering agent is a molar concentration of about $2 \times 10^{-4}$ M.

8. A formulation according to claim 6 wherein the amount of buffering agent is a molar concentration of about $4 \times 10^{-4}$ M.

9. A formulation according to claim 1 wherein the amount of oxaliplatin is from about 1 to about 7 mg/mL.

10. A formulation according to claim 1 wherein the amount of oxaliplatin is from about 1 to about 5 mg/mL.

11. A formulation according to claim 1 wherein the amount of oxaliplatin is from about 2 to about 5 mg/mL.

12. A formulation according to claim 1 wherein the amount of oxaliplatin is about 5 mg/mL.

13. A formulation according to claim 4 wherein the amount of oxaliplatin is about 5 mg/mL and the amount of buffering agent is a molar concentration of about $2 \times 10^{-4}$ M.

14. A formulation according to claim 4 wherein the amount of oxaliplatin is about 5 mg/mL and the amount of buffering agent is a molar concentration of about $4 \times 10^{-4}$ M.

15. A method for treating cancer or a solid tumor in a mammal which comprises administering to said mammal an effective amount of a formulation according to any one of claims 1–14.

16. A method for stabilizing a solution comprising a therapeutically effective amount of oxaliplatin which comprises adding an effective stabilizing amount of a buffering agent to said solution wherein the buffering agent is oxalic acid or an alkali metal salt thereof.

17. A method according to claim 16 wherein said solution is an aqueous solution and the buffering agent is oxalic acid or an alkali metal salt thereof.

18. A process for preparing a formulation according to claim 1 which comprises mixing a pharmaceutically acceptable carrier, a buffering agent and oxaliplatin.

19. A process for preparing a formulation according to claim 1 which comprises the steps of:
   (a) mixing a pharmaceutically acceptable carrier and a buffering agent;
   (b) dissolving oxaliplatin into said mixture;
   (c) cooling the mixture resulting from step (b) and making up to final volume with the pharmaceutically acceptable carrier;
   (d) filtering the solution resulting from step (c); and
   (e) optionally sterilizing the product resulting from step (d).

20. A process according to claim 19 wherein said process is carried out under an inert atmosphere.

21. A process according to claim 19 wherein the product resulting from step (d) is sterilized by exposure to heat.

22. A packaged pharmaceutical product comprising a formulation according to claim 1 in a sealable container.

23. A packaged pharmaceutical product according to claim 22 wherein the container is an ampoule, vial, infusion bag or syringe.

24. A packaged pharmaceutical product according to claim 23 wherein the container is a graduated syringe.

* * * * *